United States Patent [19]

Alfredson

[11] Patent Number: 4,476,713

[45] Date of Patent: Oct. 16, 1984

[54] LIQUID CHROMATOGRAPHIC SEPARATION OF HYDROCARBONS

[75] Inventor: Thomas V. Alfredson, San Francisco, Calif.

[73] Assignee: Varian Associates, Inc., Palo Alto, Calif.

[21] Appl. No.: 413,557

[22] Filed: Aug. 31, 1982

[51] Int. Cl.³ .............................................. G01N 31/08
[52] U.S. Cl. .................................. 73/61.1 C; 210/656
[58] Field of Search .................. 73/61.1 C; 210/198.2, 210/656; 422/70; 436/161

[56] References Cited

U.S. PATENT DOCUMENTS 3,966,596  6/1976  Stevens et al. ...................... 210/656

OTHER PUBLICATIONS

Alfredson, Thomas V., "High-Performance Liquid Chromatographic Column Switching Techniques for Rapid Hydrocarbon Group-Type Separations"; Journal of Chromatography, 218 (1981) pp. 715–728.
Matsunaga, A. et al., "Separation of Aromatic Compounds in Lubricant Base Oils by High Performance Liquid Chromatography"; Analytical Chemistry, vol. 50, No. 6, May 1978, pp. 753–756.
Mori, Sadao, "Elution Behavior of Some Solutes on a Porous Polystyrene Gel in High Performance Liquid Chromatography"; Analytical Chemistry, vol. 50, No. 6, May 1978, pp. 745–748.
Mori, S. et al., "Combination of Size Exclusion and Normal-Phase Partition Modes in High Performance Liquid Chromatography"; Analytical Chemistry, vol. 51, No. 3, Mar. 1979, pp. 382–384.
Hewlett Packard Newsletter, "High Performance Chromatography"; Avondale Division; Rt. 41; Avondale, PA 19311; vol. 3, No. 3, Jun. 1982.
Majors, Ronald E., "Recent Advances in High Performance Liquid Chromatography Packings and Columns"; Journal of Chromatographic Science, vol. 15, Sep. 1977, pp. 333–351.
Majors et al., Journal of Chromotography, 167 (1978), pp. 17–30.

*Primary Examiner*—Gerald Goldberg
*Assistant Examiner*—Joseph W. Roskos
*Attorney, Agent, or Firm*—Stanley Z. Cole

[57] ABSTRACT

There is disclosed a method for the separation and identification of components contained in hydrocarbon mixtures, such as paraffins, olefins, napthenes and/or aromatics, by liquid chromatography by use of a chromatographic column packed with a microparticulate material having a pore size of less than about 500 Å and possessing aromaticity, preferably polystyrene/divinyl benzene having a pore size of less than about 100 Å, the microparticulate material being slurry packed in a solvent medium. The hydrocarbon mixture is passed through the packed column using a mobile phase comprising a solvent having a solvent strength parameter, $\epsilon°$, of less than about 0.1 such as a $C_5$ to $C_8$ alkane; and the paraffins, olefins, napthenes, and/or aromatics are separately eluted and identified. Also disclosed is an apparatus for the characterization and separation of paraffins, olefins, napthenes, and aromatics contained in hydrocarbon mixtures, the apparatus comprising: a chromatographic column packed with a microparticulate material having a pore size of less than about 500 Å and possessing aromaticity, and slurry packed in a solvent medium; an injector for injecting a sample of the hydrocarbon mixture into said column; a solvent reservoir and pump to provide a mobile phase to the column comprising a solvent having a solvent strength parameter, $\epsilon°$, of less than about 0.1 such as a $C_5$ to $C_8$ alkane; and a detector to detect and identify the paraffins, olefins, napthenes, and aromatics as they are eluted from the column.

23 Claims, 5 Drawing Figures

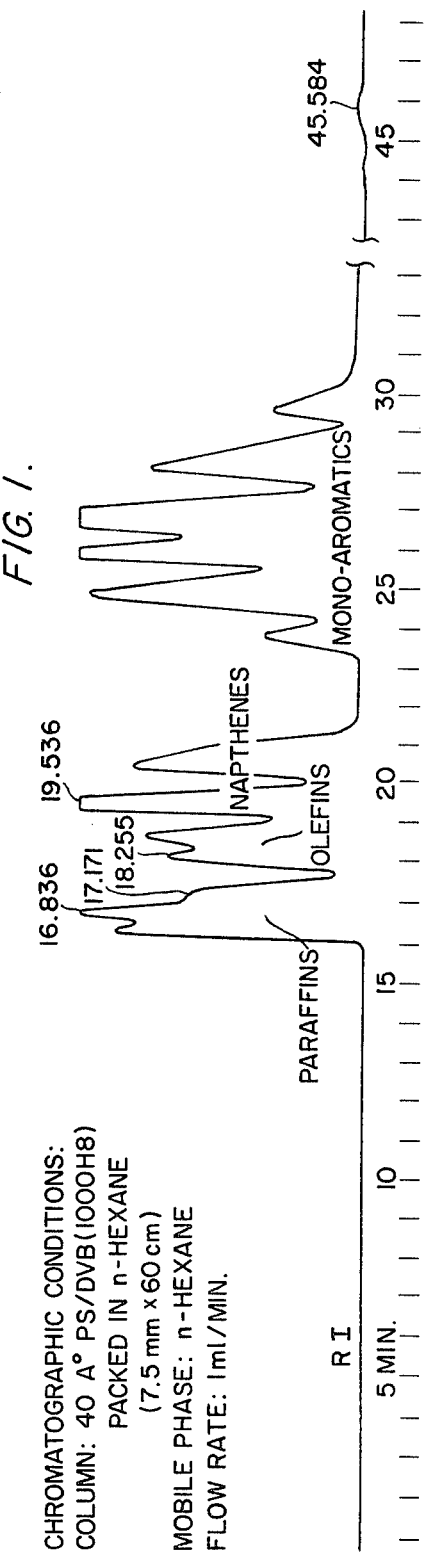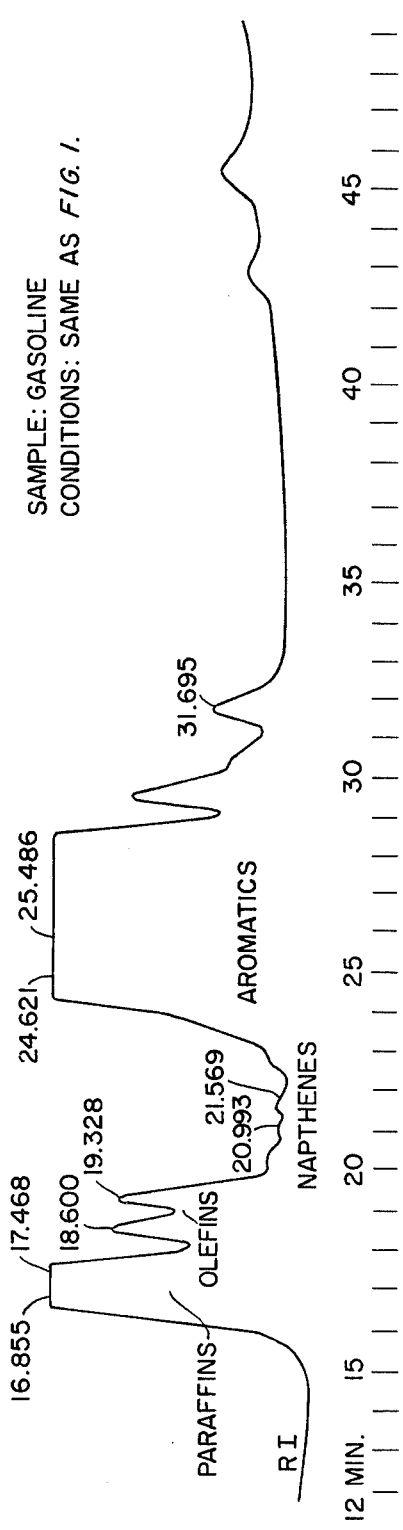

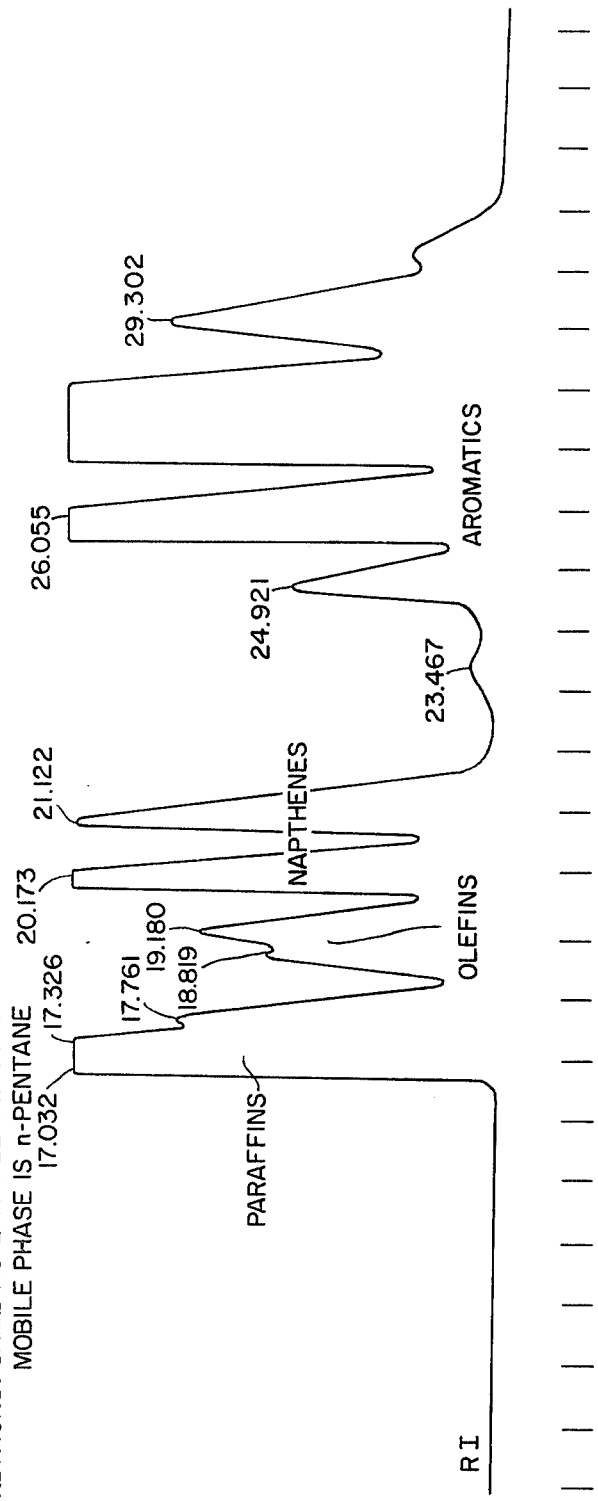

SAMPLE: REGULAR GASOLINE
CONDITIONS: SAME AS EXAMPLE 3

LIQUID CHROMATOGRAPHIC SEPARATION OF HYDROCARBONS

FIELD OF THE INVENTION

This invention relates to a process for the separation and analyses, of hydrocarbon mixtures such as petroleum samples and products containing mixtures of hydrocarbons using liquid chromatography to separate the hydrocarbon mixtures into their components.

BACKGROUND

It is well known that feed stocks and products in the petroleum industry usually occur in mixtures of difficult to separate and difficult to identify components. Accordingly, hydrocarbon group-type or class analyses is a widely used procedure for obtaining the information needed to evaluate such feed stocks and products in this industry. A general method currently in use for hydrocarbon group analyses is the fluorescent indicator adsorption (FIA) procedure which generally covers the determination of saturates, non-aromatic olefins, and aromatics in petroleum products (ASTM Standard Test Method D1319). However, limitations on this technique, such as the time required for analyses and poor precision, have led to the development of alternative methods for hydrocarbon class analyses including chromatographic methods.

High performance liquid chromatographic techniques are particularly well suited to group-type analyses because of the separation speed and ability to fingerprint most hydrocarbon classes of interest. A recent literature publication by the inventor (*Journal of Chromatography*, 218 (1981), pp 715-728) includes a listing in Table I of exemplary applications of high performance liquid chromatography techniques for separation of petroleum products. This listing includes the petroleum sample-type, column-type which may be used, the mobile phase to be used, and references in which this work was done.

In reference numbers 24 and 25, there is disclosure of work done by Matsunaga et al, *Anal. Chem.*, 50 (1978) 753-756, which includes the separation of aromatic compounds in lubricant base oils by high performance liquid chromatography. This work included the rapid class separation of aromatic compounds which are present in lubricating base stocks. These authors reported that gradient elution chromatography on activated alumina but not on silica or polystyrene gel, produces a successful separation of heavier petroleum fractions. There is no disclosure in this reference, however, for the separation of complex petroleum mixtures into its major components.

Crosslinked polystyrene-divinyl benzene (PS/DVB) exclusion packings of small pore size have been widely used in the separation of small molecules in other areas, see Majors et al., *Journal of Chromatography*, 167 (1978), pp 17-30. For example, such packings have been used for the separation and characterization of aromatic compounds in lubricant base oils as mentioned above with respect to the publications by Matsunaga et al. and an exclusion packing of this type was used in a column switching technique with other high performance liquid chromatography columns to achieve separation of paraffins, olefins, napthenes, and aromatics in gasolines. See the inventor's publication, *Journal of Chromatography*, 218 (1981) pp 715-728, mentioned above. However, in this publication, the process involves a complex multidimensional high performance liquid chromatography procedure, several columns and several switching valves in order to accomplish the results disclosed. The present invention is an improvement on the work set forth in the inventor's previous publication.

Size exclusion chromatography and normal phase partition chromatography have been performed in columns packed with styrene gels for the separation of other materials. Thus, as discussed by Mori et al., *Anal. Chem.*, Vol. 51, No. 3, March 1979, a column packed with polystyrene gel was used for application to phthalate esters, alkylbenzenes and ketones, using a chloroform/n-hexane mixture as the mobile phase. Similar work is reported by Mori in *Anal. Chem.*, Vol. 50, No. 6, May 1978, pp 745-748.

In a sales brochure available to the industry from Hewlett Packard, Avondale Division; Rt. 41; Avondale, Pa. 19311, entitled "High Resolution Chromatography", Vol. 3, No. 3, June 1982, there is an announcement of a gas chromatographic PONA (paraffin, olefin, napthene, aromatic) analyses column developed by Hewlett Packard for use in this area. This brochure indicates that this special purpose column provides type analyses using production columns to separate and identify specific components of the petroleum mixture. The columns are disclosed as containing crosslinked phases which will provide specific separation of specific components. This column, however, is not of the type used to provide a broad analyses of PONA mixtures.

SUMMARY OF THE INVENTION

It is accordingly one object of the present invention to provide a method for the separation and analyses of hydrocarbon mixtures into their major components.

A further object of the invention is to provide a method for the separation and identification of paraffins, olefins, napthenes, and aromatic components contained in hydrocarbon mixtures using high performance liquid chromatography techniques.

A still further object of the present invention is to provide a method for the separation, isolation and identification of paraffins, olefins, napthenes, and aromatics contained in petroleum feed stocks and products by the use of liquid chromatography.

A still further object of the present invention is to provide an apparatus which includes a slurry packed column which will provide rapid separation and analyses of paraffins, olefins, napthenes, and aromatics contained in hydrocarbon compositions.

Other objects and advantages of the present invention will become apparent as the description thereof proceeds.

In satisfaction of the foregoing objects and advantages there is provided by this invention a method for the separation and identification of components contained in hydrocarbon mixtures by liquid chromatography which comprises:

(a) providing a chromatographic column packed with a microparticulate material having a pore size of less than about 500 Å and possessing aromaticity, said microparticulate material being slurry packed in a solvent medium;

(b) passing said hydrocarbon mixture through said packed column using a mobile phase having a solvent strength parameter, $\epsilon°$, of less than about 0.1, such as a $C_5$ to $C_8$ alkane; and (c) eluting paraffins, olefins, napthenes, and/or aromatics from the column.

Also provided by this invention is an apparatus for the characterization and separation of paraffins, olefins, napthenes, and aromatics contained in hydrocarbon mixtures, the apparatus comprising:

(a) a chromatographic column packed with a microparticulate material having a pore size of less than about 500 Å and possessing aromaticity, said material being slurry packed in a solvent medium;

(b) injection means for injecting a sample of a petroleum mixture into said column;

(c) solvent reservoir means and pump means to provide a mobile phase having a solvent strength parameter, $\epsilon^\circ$, of less than about 0.1, such as a $C_5$ to $C_8$ alkane; and (d) detector means to detect and identify said paraffins, olefins, napthenes, and aromatics as they are eluted from said column.

BRIEF DESCRIPTION OF THE DRAWINGS

Reference is now made to the drawings accompanying the application wherein:

FIG. 1 is a graph showing analyses of a simulated mixture of a hydrocarbon using n-hexane as the mobile phase in the process of the invention;

FIG. 2 is a graph of an analyses of a gasoline sample using n-hexane as the mobile phase in the process of the invention;

FIG. 3 is a graph of the analyses of a mixture of hydrocarbon components using n-pentane as the mobile phase in the process of the invention;

DESCRIPTION OF PREFERRED EMBODIMENTS

Figure 4:
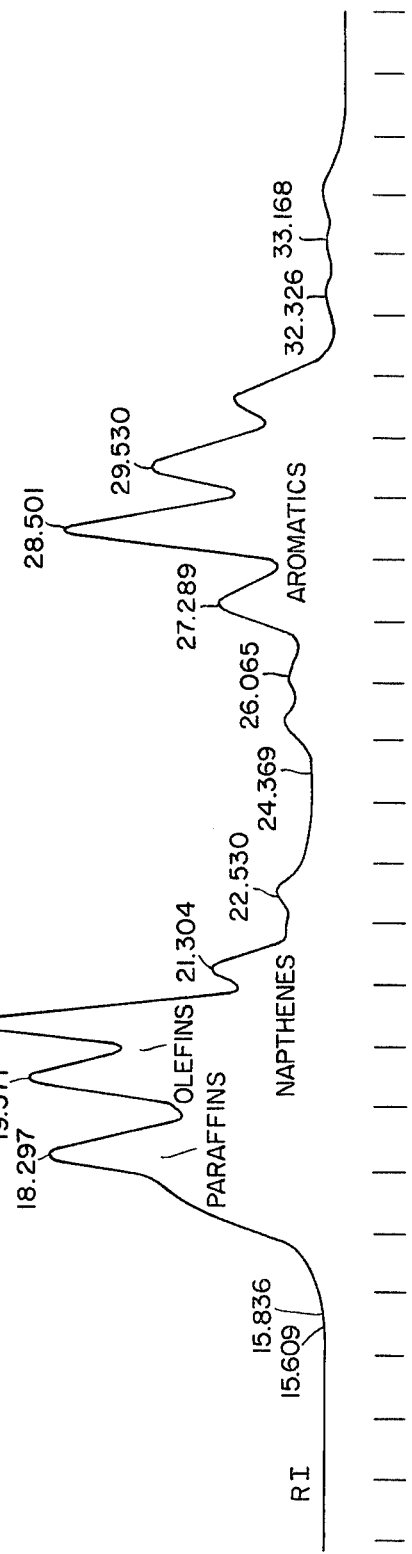
FIG. 4 is a graph of the analyses of a commercial regular grade gasoline using n-pentane as the mobile phase in the process of the invention.

As indicated above, this invention is concerned with the separation of hydrocarbon group classes, the so-called PONA assay. In this disclosure, the term "PONA" means that the hydrocarbon groups include paraffins, olefins, napthenes, and aromatics. According to this invention, petroleum compositions which contain these components can be separated and identified in a rapid and convenient manner using liquid chromatography.

Using the high performance liquid chromatography techniques of the present invention, petroleum feed stocks and other products can be separated and analyzed to obtain simultaneous class separation of paraffins (linear and branch alkanes), olefins or alkenes, napthenes (cyclic alkanes), and aromatics. The invention is based on the use of a slurry packed chromatographic column wherein the column is packed with a microparticulate material having a pore size of less than about 500 Å and which possesses aromaticity. In this system, the medium under which slurry packing occurs is a non-polar solvent and the mobile phase is a non-polar solvent, preferably a $C_5$ to $C_8$ alkane. It has been unexpectedly found according to this invention that this system will operate to provide a good separation of the components contained in these hydrocarbon mixtures. This is unexpected since column packings of this type have commonly been used with polar solvents in the separation of other materials.

The present invention satisfies a substantial need in the petroleum industry as the amounts of these hydrocarbon classes are significant and must be determined in order to evaluate the usefulness and quality of petroleum samples and products. For example, performance and specifications of many petroleum fuels and lubricants are inherently dependent upon the types of hydrocarbons present. The present invention provides a method and apparatus by which this separation and identification can be done rapidly and economically.

As is well known, petroleum products or hydrocarbon mixtures contain a wide variety of difficult to separate components. A sample of such hydrocarbon standards might include paraffins such as methyl pentane, n-hexane, trimethyl pentane, dimethyl hexane, and various other straight chain and isomeric alkanes. Napthenes which may be present include the cyclo-aliphatics such as cyclo pentane, cyclo hexane, cyclo octane, and alkyl-substituted derivatives. Olefins may include particularly the $C_5$ to $C_{10}$ series of mono-olefins as well as diolefins and isomeric derivatives. Aromatics will include benzene, toluene, the xylenes, the cymenes, and alkyl-substituted derivatives. Obviously because of the close boiling points and close molecular weights in many cases, separation is extremely difficult with any degree of rapidity and economy.

According to this invention, it has been found that if a chromatographic column is provided which is slurry packed with a microparticulate material which possesses aromaticity and a pore size of less than about 500 Å, that a rapid and economic separation can be made of the broad group of paraffins, olefins, napthenes, and aromatics. The microparticulate material is slurry packed into a chromatographic column in a non-polar solvent, preferably a $C_5$ to $C_8$ alkane such as n-pentane, n-hexane, n-heptane, or n-octane. The preferred microparticulate material will have a diameter of less than about 20 microns. In a more preferred embodiment, the diameter of the microparticulate material will be in the range of about 8–10 microns with a pore size of less than about 100 Å. It has been found that the smaller the diameter of the particulate particle, the higher the efficiency of the column.

A most preferred column packing is a commercially available material which comprises polystyrene-divinyl benzene (PS/DVB). This material is a cross-linked polystyrene-divinyl benzene microparticulate support which is available commercially for use in chromatographic columns.

While the present invention is based to some extent on the use of steric exclusion liquid chromatography as would be expected with a packing of this type, the present invention also takes advantage of adsorption chromatography so that the resulting separation is achieved through a combination of steric exclusion and adsorption chromatography. Thus, in the present invention it is theorized that the paraffins and napthenes are separated by steric exclusion, but that separation of the olefins and aromatics occur by adsorption. However, Applicant does not intend to be bound by this theory of operation of the column.

The mobile phase for use with the column is a non-polar solvent which preferably is the same as the solvent used in slurry packing of the column. Alternately, one solvent may be used for slurry packing and this solvent may be exchanged for the ultimate mobile phase solvent. This mobile phase is a non-polar solvent having a solvent strength parameter, $\epsilon^\circ$, of less than about 0.1.

Solvent strength parameter is defined in L. R. Snyder, *Principles of Adsorption Chromatography*, Chapter 8 (1976). Exemplary are the alkanes and halogenated alkanes. Preferably this is a $C_5$ to $C_8$ alkane such as n-pentane, n-hexane, n-heptane, or n-octane. N-hexane and n-pentane are the most preferred solvents to be used as the mobile phase.

The chromatographic column is usually a stainless steel column of any desired length, but usually being of less than about 100 centimeters. A preferred column size is of about 7.5 mm I.D. and 60 centimeters in length. The column is preferably packed at low pressure, i.e., less than about 7,000 psi, and in operation will be maintained from about ambient temperature up to about 40° C. The pressure in the column may range from about 1–25 atmospheres and the flow through the column will range from about 0.1 milliliter per minute to 2.0 milliliters per minute.

The microparticulate material is packed in the column as a slurry. The medium used in slurry packing of the column may be any conventional solvent medium. Suitable media include alkanes or halogenated alkanes and the like.

When the hydrocarbon sample is introduced into the column, the saturates will be resolved into the paraffins and napthenes and will be separate from the olefins. The aromatics will be resolved separately from the other groups of materials and it will be noted that the polyaromatics elute after the monoaromatics. For example, napthalene elutes after benzene.

FIGS. 1, 2, 3, and 4 which accompany this application set forth refractive index analyses of hydrocarbon mixtures which have been separated and identified using the procedure of the present invention. These analyses are more fully discussed in the following examples, but it will be generally noted from the analyses in FIGS. 1, 2, 3, and 4 that a clear separation is made between paraffins, olefins, napthenes, and aromatics and that they can be easily identified.

Figure 5:
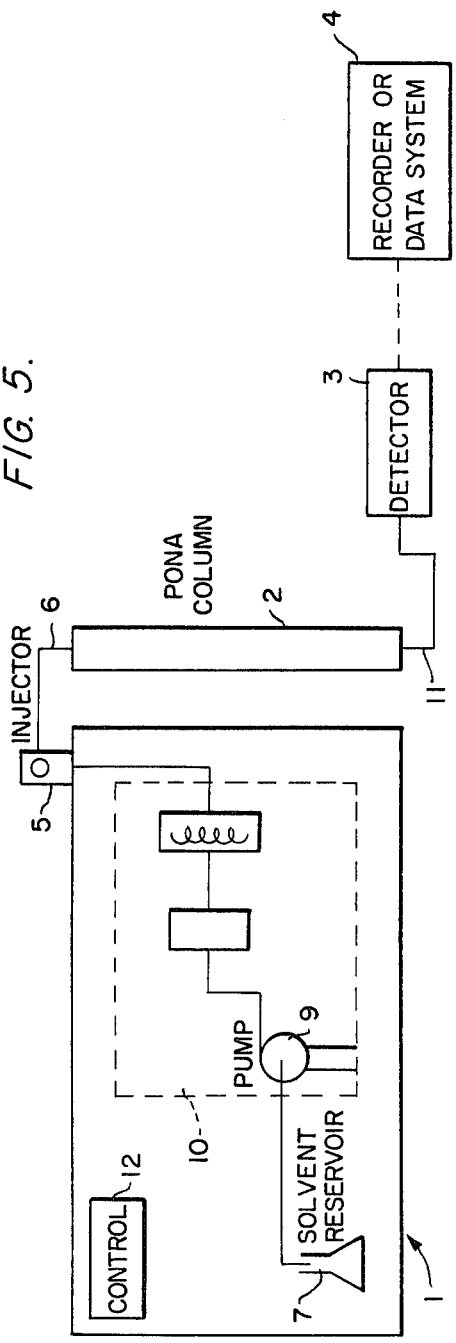
FIG. 5 is a schematic diagram of a chromatographic apparatus of the invention.

The chromatographic method and column of the present invention may be combined with an isocratic pumping system and other components of an analyzer apparatus in order to provide a self-contained analyzer for conducting a PONA analysis. Such a device is illustrated in FIG. 5 in the drawings accompanying this application. In FIG. 5 is shown a preferred embodiment of an apparatus for practicing the invention. The device of FIG. 5 is shown in simplified form including several components of chromatographs now known in the art. The novelty resides in the particular PONA column incorporated into this apparatus which distinguishes this apparatus from those now known to the art.

In the apparatus of FIG. 5 it will be seen that there is provided generally an analyzer 1, a PONA column 2, a detector 3, and a recorder or data system 4. The PONA column 2 is slurry packed with the microparticulate material having a pore diameter of less than about 500 Å as described above. The petroleum sample is introduced into injector 5 from which it is passed by line 6 into packed PONA column 2. The mobile phase such as n-hexane is contained in solvent reservoir 7 which is pumped by pump 9 to carry the sample through the column 2. The entire system is operated by hydraulic system 10 with controls 12 to maintain the system.

As the components of the sample are eluted from PONA column 2 at line 11, the detector 3 detects differences in refractive index between the mobile phase and the mobile phase which contains solute. This information is then recorded in recorder or data system 4 which may be a computer in order to identify and print out the components separated and identified in this system.

It will be understood, therefore, that this self-contained analyzer system will provide rapid and economic analysis of petroleum mixtures using the advantages provided by the chromatographic system of this invention.

Reference is now made to the following examples which illustrate specific embodiments of the present invention. In the examples and throughout the specification, parts are by weight unless otherwise indicated.

EXAMPLE I

A commercially available polystyrene-divinyl benzene packing (TSK GEL TYPE G1000H8) having a nominal pore size of 40 Å was slurry packed with reagent grade n-hexane. The column was 60 centimeters in length and 7.5 millimeters in diameter. The mobile phase was n-hexane and the flow rate was 1 milliliters/minute.

A simulated hydrocarbon sample was prepared which contained the following components:

| Paraffins | Napthenes | Olefins | Aromatics |
|---|---|---|---|
| methylpentane | cyclopentane | 1-hexene | benzene |
| n-hexane | cyclohexane | 1-heptene | toluene |
| trimethyl-pentane | cyclooctane | 1-octene | o,m-xylene |
| dimethylhexane | methylcyclo-pentane | 1-nonene | p-cymene |
| trimethylhexane | methylcyclo-hexane | 1-pentene | n-butylbenzene |
| n-nonane | | | ethylbenzene |
| n-octane | | | mesitylene |
| n-decane | | | cumene |
| n-dodecane | | | napthalene |

The sample of this hydrocarbon mixture was then introduced through the column under the conditions indicated and the components separated and identified using a refractive index detector. The results are shown in FIG. 1 accompanying the application. In FIG. 1 it will be seen that substantial and easily identifiable peaks are detected for paraffins, olefins, napthenes, and monoaromatics.

It should be noted that any detecting means can be used to identify the peaks of the components as they are eluted from the chromatographic column, such as ultraviolet, infrared or the like. However, a refractive index detector is particularly advantageous and is used in these examples.

EXAMPLE II

In this example, the same column and conditions were used as in Example I. However, the sample was a sample of a commercial grade of gasoline in which the components were unknown. The results for the analyses of the gasoline sample are set forth in FIG. 2 accompanying the application which was by refractive index detection. In this sample, it will be seen that identification of the materials eluted from the chromatographic column show significant peaks for paraffins, olefins, napthenes, and aromatics, thus indicating the components of the gasoline sample.

EXAMPLE III

In this example, a hydrocarbon standard which contains a mixture of paraffins, olefins, napthenes, and aromatics was the sample used for this experiment. Hydrocarbon standards of this type are discussed, for example, in the publication by the inventor in *Journal of Chromatography*, 218 (1981) pp 715–728. As discussed in that publication, hydrocarbon standards include model compounds for paraffins (class I), napthenes (class Ia), monoolefins (class II), diolefins (class IIa), aromatics (alkylbenzenes, class III), polynuclear aromatic hydrocarbons (PAHs, class IV) and polar (class V) hydrocarbon group-types such as those listed in Table II of the noted publication.

In this example, the apparatus used was an apparatus of the type described in FIG. 5 wherein the chromatographic column is used in combination with a refractive index detector and a recorder to provide a computer printout of the materials identified as eluted from the column. The device is also provided with an injector for the sample and a solvent reservoir with the necessary pumps and controls to inject the sample into the column and introduce the mobile phase into the column. The conditions for the experiment were generally the same as Example I in that the packing for the column was the 40 Å polystyrene/divinyl benzene microparticulate material packed in n-hexane. However, in this experiment, the mobile phase was n-pentane with the flow rate being 1.0 milliliters per minute. All other conditions were the same as in Example I.

The results of this experiment are set forth in FIG. 3 which is a printout of the peaks recorded in the refractive index detector. It will be noted particularly that significant peaks are set forth for paraffins, olefins, napthenes, and aromatics, thus demonstrating excellent separation and identification of these major components of the hydrocarbon sample subjected to the experiment.

EXAMPLE IV

In this example, the sample was regular Chevron gasoline purchased commercially and the conditions were the same as in Example III. The chromatographic column was operated in combination with apparatus as described in Example III. The mobile phase was n-pentane and the column was packed in n-hexane.

The results of this experiment are shown in FIG. 4 as a computer printout of the information obtained from the refractive index detector.

As will be seen from FIG. 4, significant peaks are shown for paraffins, olefins, napthenes, and aromatics. Thus, this experiment shows that the method and apparatus of this invention are effective to provide a rapid and meaningful separation and identification of the major components contained in the gasoline sample.

The invention has been described herein with certain preferred embodiments. However, as obvious variations thereon will become apparent to those skilled in the art, the invention is not to be considered as limited thereto.

What is claimed is:

1. A method for the separation of components contained in a hydrocarbon mixture which comprises:
   (a) providing a chromatographic column packed with a microparticulate material having a pore size of less than about 500 Å and possessing aromaticity, said microparticulate material being slurry packed in a solvent medium;
   (b) passing said hydrocarbon mixture through said packed column using a mobile phase comprising a solvent having a solvent strength parameter of less than about 0.1; and
   (c) eluting the separated components.

2. A method according to claim 1 wherein the hydrocarbon mixture contains paraffins, olefins, napthenes, and aromatics.

3. A method according to claim 1 wherein the microparticulate material has a pore size of less than about 100 Å and has a particle diameter of less than about 20 microns.

4. A method according to claim 1 wherein the flow rate of the mobile phase through the column ranges from about 0.1 milliliter per minute to 2.0 milliliters per minute in a pressure of from one atmosphere to 25 atmospheres.

5. A method according to claim 1 wherein the microparticulate material is a polystyrene/divinyl benzene particulate material.

6. A method according to claim 5 wherein the polystyrene/divinyl benzene microparticulate material has a pore size of about 40 Å and a diameter of about 8–10 microns.

7. A method according to claim 2 wherein the paraffins, olefins, napthenes, and aromatics are eluted in that order.

8. A method according to claim 1 wherein the microparticulate material is slurry packed in the column in a medium comprising n-hexane.

9. A method according to claim 8 wherein the mobile phase passed through the column is n-pentane or n-hexane.

10. A method for the separation and analyses of paraffins, olefins, napthenes, and aromatics contained in a hydrocarbon mixture using chromatographic procedures, the steps comprising:
    (a) providing a chromatographic column packed with a polystyrene/divinyl benzene microparticulate material having a pore size of less than about 100 Å, said material being slurry packed in a solvent medium;
    (b) passing said hydrocarbon mixture through said packed column using a mobile phase comprising a solvent having a solvent strength parameter, $\epsilon°$, of less than about 0.1;
    (c) eluting the paraffins, olefins, napthenes, and aromatics from said column; and
    (d) detecting the presence of said components.

11. A method according to claim 10 wherein the components are detected in step (d) by ultraviolet analyses or refractive index analyses.

12. A method according to claim 10 wherein the polystyrene/divinyl benzene microparticulate material is slurry packed in a medium comprising n-hexane.

13. A method according to claim 12 wherein the mobile phase is n-pentane or n-hexane.

14. A method according to claim 13 wherein the polystyrene/divinyl benzene microparticulate material has a pore size of about 40 Å and a diameter of about 8–10 microns.

15. A method according to claim 14 wherein the paraffins, olefins, napthenes, and aromatics are detected by refractive index analyses.

16. A method according to claim 10 wherein the flow rate of the mobile phase is about 0.1 milliliter per minute to 2.0 milliliters per minute at a pressure of about 1–25 atmospheres.

17. An apparatus for the separation and identification of components contained in hydrocarbon mixtures which comprises:
    (a) chromatographic column packed with a microparticulate material having a pore size of less than about 500 Å and possessing aromaticity, said material being slurry packed in a solvent medium;

(b) injection means for injecting a sample of the hydrocarbon mixture into said column;

(c) solvent reservoir means and pump means to provide a mobile phase to said column comprising a solvent having a solvent strength parameter, $\epsilon°$, of less than about 0.1; and (d) detector means to detect and identify the components of said hydrocarbon mixture as they are eluted from said column.

18. An apparatus according to claim 17 which includes recorder means to record the presence of the detected components.

19. An apparatus according to claim 18 wherein the detector detects the components by ultraviolet rays or refractive index.

20. An apparatus according to claim 17 wherein the microparticulate material comprises a polystyrene/divinyl benzene microparticulate packing which has a pore size of less than about 100 Å.

21. An apparatus according to claim 20 wherein the microparticulate material is slurry packed in said column in a medium comprising n-hexane and the mobile phase comprises n-pentane or n-hexane.

22. An apparatus according to claim 21 wherein the detector means detects for differences in refractive index between the eluted components.

23. An apparatus according to claim 20 wherein the polystyrene/divinyl benzene microparticulate material has a pore size of about 40 Å and a particle diameter of about 8–10 microns, the microparticulate material is packed in a medium comprising n-hexane and the mobile phase is n-hexane.

* * * * *